United States Patent [19]

Habets et al.

[11] Patent Number: 5,229,491
[45] Date of Patent: Jul. 20, 1993

[54] PEPTIDES IMMUNOCHEMICALLY REACTIVE WITH ANTIBODIES DIRECTED AGAINST HEPATITIS NON-A, NON-B VIRUS

[75] Inventors: Winand J. A. Habets, Boxtel, Netherlands; Terukatsu Arima, Kagoshima, Japan; Pieter J. Boender, Nijmegen, Netherlands

[73] Assignee: AKZO NV, Arnhem, Netherlands

[21] Appl. No.: 676,677

[22] Filed: Mar. 28, 1991

[30] Foreign Application Priority Data

Mar. 30, 1990 [EP] European Pat. Off. ........ 90200775.6

[51] Int. Cl.⁵ .................... A61K 37/02; G01N 33/543
[52] U.S. Cl. .................................. 530/326; 530/327; 530/328; 530/329; 436/518; 436/543; 436/800; 422/61; 435/1

[58] Field of Search ............. 424/88, 89; 530/326, 530/327, 328, 329; 422/61; 435/7; 436/518, 543, 800

[56] References Cited

FOREIGN PATENT DOCUMENTS 0293274 3/1988 European Pat. Off. .
0363025 4/1990 European Pat. Off. .

*Primary Examiner*—Merrell C. Cashion, Jr.
*Assistant Examiner*—Bennett Celsa
*Attorney, Agent, or Firm*—Donna Bobrowicz

[57] ABSTRACT

The invention concerns peptides which react immunochemically with antibodies directed against NANBH. A method for the detection of NANBH or anti-NANBH in a test fluid, an immunochemical reagent and a testkit to be used when applying said detection methods belong to the invention.

4 Claims, No Drawings

PEPTIDES IMMUNOCHEMICALLY REACTIVE WITH ANTIBODIES DIRECTED AGAINST HEPATITIS NON-A, NON-B VIRUS

The invention relates to peptides which react immunochemically with antibodies directed against hepatitis Non-A, Non-B virus (NANBH-virus).

The invention further relates to a method for the detection of NANBH or anti-NANBH in a test fluid, and to an immunochemical reagent and a test kit to be used when applying the said detection method.

Non-A, Non-B hepatitis, which may or may not be caused by Hepatitis C Virus (HCV), is a transmissible disease or family of diseases shown to be virus-induced. It can be distinguished from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). NANBH was first identified in transfused individuals. Transmission from man to chimpanzee and serial passage in chimpanzees provided evidence that NANBH is due to a transmissible infectious agent or agents.

Epidemiologic evidence is suggestive that there may be three types of NANBH: the water-borne epidemic type; the blood or needle associated type; and the sporadically ocurring (community acquired) type. However, the number of agents which may be the causative of NANBH is unknown.

Clinical diagnosis and identification of NANBH has been accomplished primarily by exclusion of other viral markers. Among the methods used to detect putative NANBH antigens and antibodies are agar-gel diffusion, counter-immunoelectrophoresis, immunofluorescence microscopy, immune electron microscopy, radioimmunoassay, and enzyme-linked immunosorbent assay. However, none of these assays has proved to be sufficiently sensitive, specific, and reproducible to be used as a diagnostic test for NANBH.

However, for the development of a specific and sensitive method to enable a reliable diagnosis to be made in various phases of the infection with NANBH it is of great importance to identify immuno-dominant viral epitopes of this type.

A peptide has now been found with 15 amino acids and an amino acid sequence as shown in FIG. 1 which are exceptionally immunochemically reactive with NANBH antibodies.

The invention also includes fragments of the said pentadecapeptide which are still immunochemically reactive with NANBH-antibodies and also polypeptides which contain the said pentadecapeptide as an essential constituent, or fragments thereof which are immunochemically reactive with NANBH-antibodies.

The nonapeptide with amino acid sequence Arg-Lys-Thr-Lys-Arg-Ser-Thr-Asn-Arg is preferred as fragment of the pentadecapeptide according to the invention.

The invention also relates to an immunochemical reagent, which reagent contains at least one of the peptides according to the invention.

The invention also comprises a method for the detection of antibodies directed against NANBH in a test fluid, using at least one of the peptides according to the invention.

The invention also relates to a method for the detection of NANBH in a test fluid, using at least one of the peptides according to the invention.

Finally, the invention relates to a test kit to be used for carrying out an immuno-assay, this test kit containing at least one immunochemical reagent according to the invention.

The peptides mentioned above are particularly suitable for use in a diagnostic method for the determination of the presence of NANBH or NANBH-antibodies in a test fluid.

In contrast to the natural NANBH, the peptides according to the invention have the great advantage that these are of a safe non-infectious origin.

The preparation of the peptides according to the invention is effected by means of one of the known organic chemical methods for peptide synthesis or with the aid of recombinant DNA techniques. This latter method involves the preparation of the desired peptide by means of bringing to expression a recombinant polynucleotide with a polynucleotide sequence which is coding for one or more of the peptides in question in a suitable micro-organism as host.

The organic chemical methods for peptide synthesis are considered to include the coupling of the required amino acids by means of a condensation reaction, either in homogeneous phase or with the aid of a so-called solid phase.

The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent, b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1-3 (Ed. Gross, E. and Meienhofer, J.) 1979, 1980, 1981 (Academic Press, Inc.).

Preparation of the abovementioned peptides according to the invention using the "solid phase" is for instance described in J. Amer. Chem. Soc. 85, 2149 (1963) and Int. J. Peptide Protein Res. 35, 161-214 (1990). The coupling of the amino acids of the peptide to be prepared usually starts from the carboxyl end side. For this method a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl or aminefunction.

A particularly suitable solid phase is, for example, the p-alkoxybenzyl alcohol resin (4-hydroxy-methyl-phenoxy-methyl-copolystrene-1% divinylbenzene resin), described by Wang (1974) J. Am. Chem. Soc. 95.

1328. After synthesis the peptides can be split from this solid phase under mild conditions.

After synthesis of the desired amino acid sequence, detaching of the peptide from the resin follows, for example, with trifluoromethanesulphonic acid or with methanesulphonic acid dissolved in trifluoroacetic acid. The peptide can also be removed from the carrier by transesterification with a lower alcohol, preferably methanol or ethanol, in which case a lower alkyl ester of the peptide is formed directly. Likewise, splitting with the aid of ammonia gives the amide of a peptide according to the invention.

The reactive groups which may not participate in the condensation reaction are, as stated, effectively protected by groups which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups which can effectively protect an amino group are the ethoxycarbonyl, benzyloxycarbonyl, t-butoxycarbonyl or p-methoxy-benzyloxycarbonyl group, or an acid group derived from a sulphonic acid, such as the benzene-sulphonyl or p-toluene-sulphonyl group, but other groups can also be used, such as substituted or unsubstituted aryl or aralkyl groups, for example benzyl and triphenylmethyl, or groups such as ortho-nitrophenyl-sulphenyl and 2-benzoyl-1-methyl-vinyl. A particularly suitable α-amino-protective group is, for example, the base-sensitive 9-fluorenylmethoxycarbonyl (Fmoc) group [Carpino & Han (1970) J. Amer. Chem. Soc. 92, 5748].

A more extensive account of possible protecting groups can be found in The Peptides, Analysis, Synthesis, Biology, Vol. 1-9 (Eds. Gross, Udenfriend and Meienhofer) 1979-1987 (Academic Press, Inc.).

It is necessary also to protect the ε-amino group of lysine and advisable for the guanidine group of arginine. Customary protective groups in this connection are a Boc-group for lysine and a Pmc- or Pms- or Mbs-group or Mtr-group for arginine.

The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

As already indicated above, the peptide according to the invention can likewise be prepared with the aid of recombinant DNA techniques. This possibility is of importance particularly when the peptide is incorporated in a repeating sequence ("in tandem") or when the peptide can be prepared as a constituent of a (much larger) protein or polypeptide. This type of preparation of the peptide therefore likewise falls within the scope of the invention. For this purpose, as a constituent of a recombinant DNA, a polynucleotide is used which codes for the peptide according to the invention and which, furthermore, is substantially free from polynucleotide segments, which in the naturally occurring NANBH genome flank the polynucleotide sequence indicated above.

A polynucleotide of this type, which is coding for the peptide according to the invention, and a recombinant DNA in which this polynucleotide is incorporated likewise fall within the scope of the invention.

Without this specifically being incorporated in the claims, it is self-evident that one or more aminoacids in the peptides according to the invention can be replaced by other aminoacids.

In addition the functional derivatives of these peptides, by which are meant in the main:
(a) acid addition salts of the peptides;
(b) amides of the peptides and specifically the C-terminal amides;
(c) esters and specifically C-terminal esters and
(d) N-acyl derivatives, specifically N-terminal acyl derivatives and in particular N-acetyl derivatives, are also considered as peptides according to the invention.

The "immunochemical reagent" according to the invention usually consists of one or more peptides according to the invention and a suitable support or a labelling substance.

Supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle, a carrier protein such as BSA or KLH.

Labelling substances which can be used are, inter alia, a radioactive isotope, a fluorescent compound, an enzyme, a dye sol, metal sol or metal compound as sol particle.

In a method for the detection of antibodies directed against NANBH in a test fluid, an immunochemical reagent according to the invention is brought into contact with the test fluid. After which, the presence of immune complexes formed between the peptide and antibodies in the test fluid is detected, and by this detection the presence of NANBH antibodies in the test fluid is known and can be determined quantitatively.

Depending on the nature and further characteristics of the immunochemical reagent the immunochemical reaction that takes place is a so-called sandwich reaction, an agglutination reaction, a competition reaction or an inhibition reaction.

For the detection of NANBH in a test fluid an immunochemical reagent according to the invention is brought into contact with the test fluid and anti-NANBH after which the presence of immune complexes formed is detected and, from this, the presence of NANBH in a test fluid can be determined.

A particularly suitable method for the detection of NANBH in a test fluid is based on a competition reaction between a peptide according to the invention provided with a labelling substance and a NANBH antigen (present in the test fluid) whereby the peptide and the antigen are competing with the antibody directed against NANBH attached to a solid support.

A test kit according to the invention comprises, as an essential constituent, an immunochemical reagent as described above. Carrying out a sandwich reaction for the detection of NANBH antibodies the test kit may comprise, for example, the peptide according to the invention coated to a solid support, for example the inner wall of a microtest well, and either a labelled peptide according to the invention or a labelled anti-antibody.

For carrying out a competition reaction, the test kit may comprise the peptide according to the invention coated to a solid support and a labelled antibody directed against NANBH preferably a monoclonal antibody directed against said peptide.

In an agglutination reaction the test kit comprises an immunochemical reagent which consists of a peptide according to the invention coated to particles or sols.

A test kit for the detection of NANBH antigen comprises for example a labelled peptide according to the invention and an antibody directed against NANBH, which is coated to a solid support.

EXAMPLE I

The pentadecapeptide with the sequence as shown in FIG. 1 was prepared by stepwise solid phase peptide synthesis. The synthesis was carried out using a VEGA Coupler 250 C automated peptide synthesizer or a Labortec SP640 semi-automatic peptide synthesizer, employing a p-benzyloxybenzyl alcohol resin (Wang-resin; 0.6–0.7 mmoles/g, Bachem AG, Switzerland) and $N^\alpha$-Fmoc-protected (Fmoc, 9-fluorenyl-methyloxycarbonyl) amino acids.

The synthesis started by the coupling of Fmoc-Arg(Pmc)-OH to the resin using DCC (dicyclohexyl-carbodiimide, 1 equivalent), HOBt (1-hydroxybenzotriazole, 2 equivalents) and DMAP (N,N-dimethylaminopyridine, 1 equivalent) in DMF-dichloromethane (1:1, vol/vol) at 4° C. for 18 hours. Unreacted alcohol functions on the resin were then blocked by benzoylation using benzoylchloride-pyridine for 2 hours.

The resulting Fmoc-Arg(Pmc)-resin (0.38 mmol/g) was successively treated three times with 20% piperidine in DMF for 6 min, in order to remove the Fmoc-group. The protected pentadecapeptide was then prepared on the H-Arg(Pmc)-resin by successive coupling steps of the Fmoc-amino acids, as dictated by the amino acid sequence. The following side chain protecting groups were used: -Pmc (2,2,5,7,8-pentamethylchroman-6-sulfonyl-) for Arg; -tBu (tert.butyl-) for Thr and Ser; Boc(t-butyloxycarbonyl) for Lys and Trt (trityl) for Asn and Gln.

Each coupling step was performed using 3 equivalents each of Fmoc-amino acid, BOP (=benzotriazolyloxy-tris(dimethylamino)-phosphonium hexafluorophosphate), HOBt and 4,5 equivalents of DIPEA (=N,N-diisopropyl-ethylamine) in 12–15 ml of DMF per gram resin for 15 min, followed by 3 cycles of washings (one min each) with DMF and ethanol. Completeness of the coupling reaction was monitored by the ninhydrin test of Kaiser (Anal. Biochem. 34, 595–598, 1970). A positive ninhydrin reaction was observed following coupling of $Ser^{10}$ and $Arg^5$. In each case the coupling reaction was repeated once using one equivalent of corresponding Fmoc-amino acid, BOP, HOBt and DIPEA for 30 min. Any remaining free amino groups were then blocked by acetylation using acetic anhydride-DMF (5:95; vol/vol) for 10 min and subsequent washings with DMF and ethanol (1 min each), respectively.

After each synthesis cycle the $N^\alpha$-Fmoc-protecting group was removed by treatment with 25% piperidine in DMF as described above.

After completion of the synthesis, the resulting fully protected pentadecapeptide resin was treated in a mixture of trifluoro acetic acid-water-phenol-thioanisole-ethanedithiol (82:5:5:5:2,5 vol/vol) for 18 hours at room temperature, in order to effect release of the peptide from the resin with simultaneous removal of all protecting groups. The cured peptide was isolated following precipitation upon addition of the reaction mixture to diethyl ether. The pentadecapeptide was purified by HPCL on $C_{18}$-silica using a gradient of acetonitrile in 0.1M phosphate buffer at pH 2.1.

EXAMPLE II

The pentadecapeptide with the aminoacid sequence as shown in FIG. 1 was dissolved to 7.5 μg/ml in 100 mM phosphate buffer pH 8.0. Microtiter plates where pre-treated with 0.2% glutar aldehyde in phosphate buffer pH 5.0 at 135 μl per well for 4 h at room temperature under continuous shaking. Plates were then emptied and 135 μl of the above peptide solution was given to each well. Binding of the peptide to the microtiter plate was allowed to proceed for 3 h at 37° C. The plates were frozen and stored overnight at −20° C.

Subsequently the plates were thawed and emptied, and residual binding sites were blocked with a solution of 0.05% Tween 20$^{(R)}$ in 0.2M Tris pH 7.4/0.2M NaCl for 5 min. at room temperature. Plates were then washed once with 0.2M Tris pH 7.4/0.2M NaCl and twice with 0.04M Tris pH 7.4, at 250 μl per well. For the determination of antibodies specific for Non-A, Non-B hepatitis, the serum sample was diluted in sample diluent (phosphate buffered saline (PBS)/20% normal goat serum/1% Triton X1000) pipetted into the well (100 μl per well) and incubated a for 1 h at 37° C. After washing the wells the PBS/0.05% Tween 20$^{(R)}$ the bound human antibodies were detected with goat anti-human immunoglobulin labeled with peroxidase (100 μl per well, 1 h at 37° C.) diluted in sample diluent. The plates were washed 4 times with PBS/0.05% Tween 20$^{(R)}$. TMB was added (100 μl per well) as a substrate for the peroxidase enzyme and the reaction was allowed to proceed for 30 min. at room temperature. The reaction was stopped by adding 100 μl 2M $H_2SO_4$ to each well. The yellow color was read at 450 nm in an Organon Teknika microelisa reader.

With sera from patients with Non-A, Non-B hepatitis, extinctions ranging form 1.8 to 3.0 were measured whereas the mean extinction of 20 normal human sera was 0.301 (standard deviation 0.07). As a control, the procedure was repeated with two unrelated pentadecapeptide. In both cases, no significant differences were observed in the extinctions obtained with normal human sera and serum samples form patients with NANBH.

EXAMPLE III

Fragment of the pentadecapeptide shown in FIG. 1 were also tested for reactivity with sera from patients with NANBH.

The nonapeptides 2 to 8 shown below and on the next page were synthesized and coupled to a solid support essentially as described in examples I and II. Immune reactivity with serum samples obtained from patients with NANBH was established as described in example II. The nonapeptides 5, 6 and 7 specifically reacted with antibodies in sera from patients with NANBH. These results are summarized in table 1.

TABLE 1

| Peptide | Highest/lowest $E_{450}$ obtained with NANBH-sera | Mean $E_{450}$ obtained with 20 normal human sera ± S.D. |
|---------|---------------------------------------------------|----------------------------------------------------------|
| 2 | 0.27/0.19 | 0.21 ± 0.02 |

TABLE 1-continued

| Peptide | Highest/lowest $E_{450}$ obtained with NANBH-sera | Mean $E_{450}$ obtained with 20 normal human sera ± S.D. |
|---------|---------------------------------------------------|----------------------------------------------------------|
| 3 | 0.24/0.14 | 0.22 ± 0.02 |
| 4 | 0.29/0.12 | 0.24 ± 0.02 |
| 5 | 1.30/1.10 | 0.26 ± 0.02 |
| 6 | 1.95/1.45 | 0.22 ± 0.02 |
| 7 | 1.65/1.02 | 0.21 ± 0.02 |
| 8 | 0.20/0.09 | 0.20 ± 0.02 |

Arg—Thr—Gln—Gln—Arg—Lys—Thr—Lys—Arg
Amino acid sequence of peptide 2.
Thr—Gln—Gln—Arg—Lys—Thr—Lys—Arg—Ser
Amino acid sequence of peptide 3.
Gln—Gln—Arg—Lys—Thr—Lys—Arg—Ser—Thr
Amino acid sequence of peptide 4.
Gln—Arg—Lys—Thr—Lys—Arg—Ser—Thr—Asn
Amino acid sequence of peptide 5.
Arg—Lys—Thr—Lys—Arg—Ser—Thr—Asn—Arg
Amino acid sequence of peptide 6.
Lys—Thr—Lys—Arg—Ser—Thr—Asn—Arg—Arg
Amino acid sequence of peptide 7.
Thr—Lys—Arg—Ser—Thr—Asn—Arg—Arg—Arg
Amino acid sequence of peptide 8.

We claim:

1. A polypeptide consisting essentially of a pentadecapeptide with the amino acid sequence Arg-Thr-Gln-Gln-Arg-Lys-Thr-Lys-Arg-Ser-Thr-Asn-Arg-Arg-Arg (SEQ. ID. No. 1) or fragments thereof containing the sequence -Lys-Thr-Lys-Arg-Ser-Thr-Asn- and which are immunochemically reactive with anti-non-a, non-b hepatitis antibodies.

2. An article comprising a polypeptide according to claim 1 bound to a solid support selected from the group consisting of a test tube, a membrane, a filter, a particle, an erythrocyte, a sol particle and a carrier protein.

3. A test kit to be used in an immunoassay, comprising the article according to claim 2.

4. A polypeptide according to claim 1, wherein said polypeptide is labelled with a substance selected from the group consisting of a radioactive isotope, a fluorescent compound, an enzyme, a dye sol, and a metal sol.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Arg  Thr  Gln  Gln  Arg  Lys  Thr  Lys  Arg  Ser  Thr  Asn  Arg  Arg  Arg
 1             5                        10                            15
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Arg  Thr  Gln  Gln  Arg  Lys  Thr  Lys  Arg
 1                      5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Thr  Gln  Gln  Arg  Lys  Thr  Lys  Arg  Ser
 1                      5
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
        Gln Gln Arg Lys Thr Lys Arg Ser Thr
        1               5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
        Gln Arg Lys Thr Lys Arg Ser Thr Asn
        1               5
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
        Arg Lys Thr Lys Arg Ser Thr Asn Arg
        1               5
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
        Lys Thr Lys Arg Ser Thr Asn Arg Arg
        1               5
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
        Thr Lys Arg Ser Thr Asn Arg Arg Arg
        1               5
```